United States Patent [19]

Marzolph et al.

[11] Patent Number: 4,666,935
[45] Date of Patent: May 19, 1987

[54] SUBSTITUTED MALEIMIDES AND THEIR USE AS FUNGICIDES FOR PLANT-PATHOGENIC FUNGI

[75] Inventors: Gerhard Marzolph, Cologne; Heinz U. Blank, Odenthal; Paul Reinecke, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 578,231

[22] Filed: Feb. 8, 1984

[30] Foreign Application Priority Data

Feb. 25, 1983 [DE] Fed. Rep. of Germany ....... 3306697

[51] Int. Cl.$^4$ .................. C07D 207/448; A01N 37/32
[52] U.S. Cl. .................................... 514/424; 548/548
[58] Field of Search ................. 548/548, 549; 514/424

[56] References Cited

U.S. PATENT DOCUMENTS 2,962,504 11/1960 Walker et al. ...................... 548/548
3,129,225 4/1984 Shapiro et al. ..................... 544/141
3,337,584 8/1967 Knock ................................. 548/548
3,734,927 5/1973 Kawada et al. .

FOREIGN PATENT DOCUMENTS 0045907 2/1982 European Pat. Off. .
0098953 1/1984 European Pat. Off. .
57-122065 7/1982 Japan .................................. 548/547
880555 10/1961 United Kingdom .
2087879 6/1982 United Kingdom .

OTHER PUBLICATIONS

Abstract Japanese Patent 78027336, Agricultural Chemistry–p. 2, vol. 78, No. 32.

Primary Examiner—Glennon H. Hollrah
Assistant Examiner—D. B. Springer
Attorney, Agent, or Firm—Sprung Horn Kramer & Woods

[57] ABSTRACT

Substituted maleimides of the formula

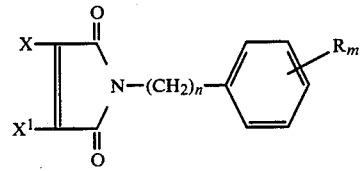

in which
  X represents hydrogen, chlorine or bromine,
  $X^1$ represents chlorine or bromine,
  n represents 2, 3, 4 or 5 and
  R represents halogen, alkyl, optionally substituted aryl, aryloxy or cycloalkyl, halogenoalkyl, hydroxyalkyl, alkoxyalkyl, acyloxyalkyl, nitro, cyano, alkoxycarbonyl, alkylcarbonyl, carboxyl, carbonylamino, hydroxyl, alkoxy, halogenoalkoxy, acyloxy, sulphonylamino, alkylsulphonyl, alkylmercapto, marcapto, acylmercapto, halogenoalkylmercapto, amino, mono- or di-alkylamino or acylamino and
  m represents 1, 2, 3, 4 or 5,
which possess fungicidal activity.

13 Claims, No Drawings

SUBSTITUTED MALEIMIDES AND THEIR USE AS FUNGICIDES FOR PLANT-PATHOGENIC FUNGI

The present invention relates to new substituted maleimides, several processes for their preparation and their use as agents for combating pests.

It is already known that N-aryl-maleimides, such as, for example, 2,3-dichloromaleic acid N-(4-fluorophenyl)-imide, have fungicidal properties (compare U.S. Pat. No. 3,734,927).

N-aralkyl-maleimides, such as, for example, maleic acid N-(2-phenyl-ethyl)-imide, which are used as seed dressing agents are also known (compare Japanese Patent Application No. 78-27,336).

New substituted maleimides of the formula (I)

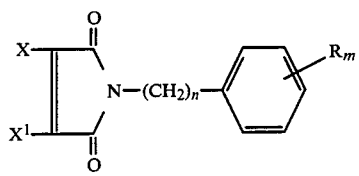

in which
X represents hydrogen, chlorine or bromine,
$X^1$ represents chlorine or bromine,
n represents 2, 3, 4 or 5 and
R represents halogen, alkyl, optionally substituted aryl, aryloxy or cycloalkyl, halogenoalkyl, hydroxyalkyl, alkoxyalkyl, acyloxyalkyl, nitro, cyano, alkoxycarbonyl, alkylcarbonyl, carboxyl, carbonylamino, hydroxyl, alkoxy, halogenoalkoxy, acyloxy, sulphonylamino, alkylsulphonyl, alkylmercapto, mercapto, acylmercapto, halogenoalkylmercapto, amino, mono- or di-alkylamino or acylamino and
m represents 1, 2, 3, 4, or 5,
have been found.

It has furthermore been found that the substituted maleimides of the formula (I)

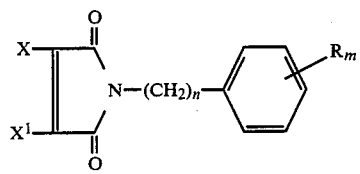

in which
X represents hydrogen, chlorine or bromine,
$X^1$ represents chlorine or bromine,
n represents 2, 3, 4 or 5,
R represents halogen, alkyl, optionally substituted aryl, aryloxy or cycloalkyl, halogenoalkyl, hydroxyalkyl, alkoxyalkyl, acyloxyalkyl, nitro, cyano, alkoxycarbonyl, alkylcarbonyl, carboxyl, carbonylamino, hydroxyl, alkoxy, halogenoalkoxy, acyloxy, sulphonylamino, alkylsulphonyl, alkylmercapto, mercapto, acylmercapto, halogenoalkylmercapto, amino, mono- or di-alkylamino or acylamino and
m represents 1, 2, 3, 4 or 5,
are obtained by a process in which
(a) A halogenomaleic anhydride of the formula (II)

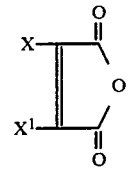

in which X and $X^1$ have the abovementioned meaning, is reacted with primary amines of the formula (III)

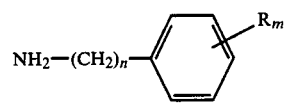

in which R, m and n have the abovementioned meaning, in a diluent, or
(b) A dialkyl halogenomaleate of the formula (IV)

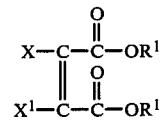

in which X and $X^1$ have the abovementioned meaning and $R^1$ represents alkyl, is reacted with primary amines of the formula (III) in which R, m and n have the abovementioned meaning, if appropriate in a solvent or diluent, or (c) halogenomaleic acid monoamides of the formula (V)

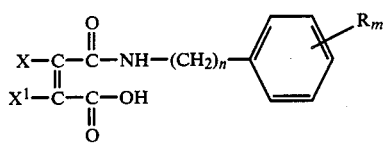

in which X, $X^1$, R, m and n have the abovementioned meaning, are cyclized to the compounds of the formula (I) in the presence of a solvent, such as, for example, glacial acetic acid, and if appropriate of a dehydrating agent, such as, for example, acetic anhydride or thionyl chloride.

The new substituted maleimides have powerful fungicidal properties. Surprisingly, the compounds of the formula (I) according to the invention thereby display a considerably more powerful action than the compounds known from the prior art which are closely related compounds from the point of view of their action.

The invention preferably relates to those substituted maleimides of the formula (I) in which
X represents hydrogen, chlorine or bromine,
$X^1$ represents chlorine or bromine,
n represents 2, 3 or 4,
R represents halogen, alkyl with 1 to 6 carbon atoms, or aryl, cycloalkyl or aryloxy which is optionally mono-, di-, tri-, tetra- or penta-substituted by identical or different halogen or alkyl radicals, or alkoxy, alkoxycarbonyl, alkylcarbonyl or alkylsulphonyl with 1 to 5 carbon atoms per alkyl radical, or carboxyl, carbonylamino, sulphonylamino, nitro, cyano, hydroxyl, halogenoalkyl with 1 to 7 halogen atoms and 1 to 4 carbon atoms per alkyl radical, acyloxy or acylamino with 1 to 5 carbon atoms per acyl radical, amino or mono- or di-alkylamino with 1 to 4 carbon atoms per alkyl radical and m represents 1, 2, 3, 4 or 5.

Particularly preferred substituted maleimides of the formula (I) are those in which X represents halogen, chlorine or bromine, $X^1$ represents chlorine or bromine, n represents 2, 3 or 4, R represents fluorine, chlorine, bromine, alkyl with 1 to 5 carbon atoms, alkoxy with 1 to 4 carbon atoms, sulphonylamino, alkylsulphonyl or alkylcarbonyl with 1 to 3 carbon atoms in the alkyl part, carbonylamine, halogenoalkyl with 1 to 3 carbon atoms and 1 to 5 halogen atoms, phenyl, chlorophenyl, cyclopentyl or cyclohexyl, alkoxycarbonyl with 1 to 4 carbon atoms in the alkoxy part, hydroxyl, acyloxy or acylamino with 1 to 3 carbon atoms per acyl radical, amino, mono- or di-alkylamino with 1 to 3 carbon atoms per alkyl radical or nitro and m represents 1, 2, 3, 4 or 5.

Very particularly preferred substituted maleimides of the formula (I) are those in which X and $X^1$ represent chlorine or bromine, n represents 2 or 3, R represents fluorine, chlorine, bromine, methyl, ethyl, n-propyl, iso-propyl, n-butyl, sec.-butyl, iso-butyl or tert.-butyl, methoxy, ethoxy, n-propoxy or iso-propoxy, sulphonylamino, methylsulphonyl, ethylsulphonyl, n-propylsulphonyl, iso-propylsulphonyl, methylcarbonyl, ethylcarbonyl, n-propylcarbonyl or iso-propylcarbonyl, carbonylamine, trifluoromethyl, phenyl, cyclopentyl or cyclohexyl, methoxycarbonyl, ethoxycarbonyl, n-propoxycarbonyl or iso-propoxycarbonyl, hydroxyl, formyloxy, acetoxy, formylamino or acetamino, amino, methylamino, dimethylamino, ethylamino, diethylamino or nitro and m represents 1, 2 or 3.

If, for example, dibromomaleic anhydride and 3-(4-chlorophenyl)-propylamine are used for process variant (a), the course of the reaction can be represented by the following equation:

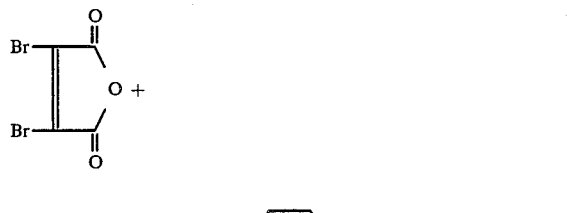

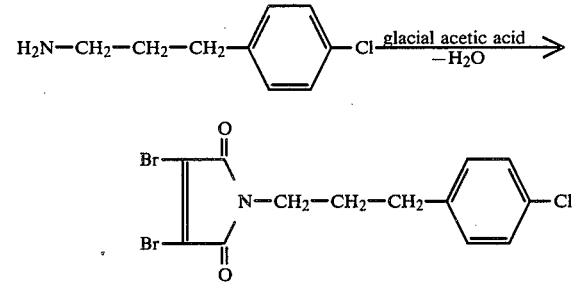

If dimethyl dichloromaleate and 2-(3-trifluoromethylphenyl)-ethylamine are used as starting substances in process variant (b), the course of the reaction can be represented by the following equation:

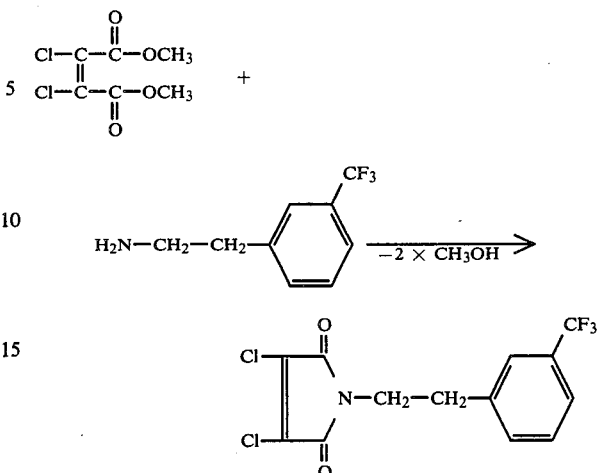

If dichloromaleic anhydride and 2-(2-chlorophenyl)-ethylamine are used as starting substances in process variant (c), the dichloromaleic acid monoamides are obtained, and are cyclized. This course of the reaction can be represented by the following equation:

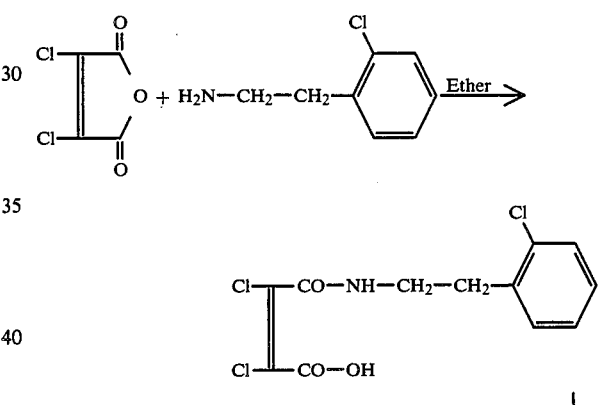

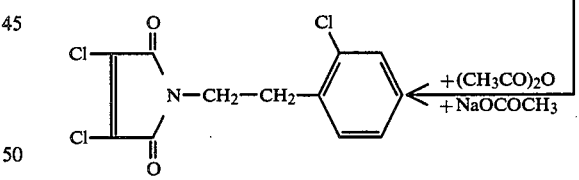

Formula (II) provides a general definition of the halogenomaleic anhydrides required as starting compounds in carrying out process variant (a). These compounds are commercially obtainable as acids or anhydrides and/or can be prepared by known processes. Formula (III) provides a definition of the amines also to be used in process variants (a) and (b). In this formula, the radicals have the meaning which has already been given in connection with the description of the substances of the formula (I) according to the invention. The amines are known in some cases, or they can be prepared by generally known processes. Thus, for example, the amines can be prepared by reducing nitriles or aldoximes with hydrogen (compare Houben-Weyl, Methoden der organischen Chemie [Methods of Organic Chemistry], XI/1, pages 341 et seq.). Reductive amination of aldehydes with hydrogen and ammonia is also a current method (compare Houben-Weyl, XI/1, page 341). The method of reduction of ω-nitrostyrenes with complex hydrides is suitable, above all, for the preparation of phenylethylamines (compare Canad. J. of Chem. 51, 1973, page 1402).

Formula (IV) describes the dialkyl halogenomaleates also required in process variant (b). These esters are known and can be obtained by current processes from the commercially available halogenomaleic anhydrides by reaction with alcohols.

The halogenomaleic acid monoamides of the formula (V) to be used in process variant (c) are known in some cases, or they can be prepared by processes which are known per se from the corresponding maleic anhydrides by reaction with primary amines (compare Organic Synthesis 41, page 93 (1961)).

Possible diluents for process variant (a) are, above all, carboxylic acids, such as, for example, formic acid, acetic acid and propionic acid.

Possible diluents in process variant (b) are organic solvents. These include, preferably, toluene, xylene, chlorobenzene, perchloroethane, dioxane, glycol dimethyl ether and dimethylformamide.

The following diluents are preferably used in process variant (c): carboxylic acids, such as acetic acid; aromatic hydrocarbons, such as toluene or xylene; halogenohydrocarbons, such as chlorobenzene; and furthermore dioxane, and dehydrating agents which are preferably used are acetic anhydride, phosgene, thionyl chloride, phosphorus oxychloride and phosphorus pentachloride.

The reaction temperatures can be varied within a substantial range in carrying out the different process variants. The reaction is carried out at temperatures from 20° to 150° C., preferably 80° to 120° C., in process variant (a). In process variant (b), the reaction is carried out at temperatures from 50° to 180° C., preferably 80° to 130° C., and in process variant (c) the reaction is carried out at temperatures from 0° to 150° C., preferably 50° to 120° C.

All three variants are in general carried out under normal pressure.

Equimolar amounts of the starting substances are preferably employed in carrying out all the process variants.

The amines of the formula (III) can be used as free bases or in the form of their salts, such as, for example, the hydrochlorides, hydrobromides, acetates or oxalates.

If the amines of the formula (III) are used in the form of their salts, a corresponding, for example equimolar, amount of an auxiliary base, such as, for example, triethylamine or sodium acetate, is advantageously added to the reaction mixture.

According to a preferred embodiment of process variant (a), equimolar amounts of the starting substances are stirred in an organic solvent, for example glacial acetic acid, at elevated temperature for several hours. The mixture is then cooled to room temperature and water is added, whereupon the product already precipitates.

If dibromomaleic anhydride is used as the starting substance, in a preferred embodiment this is prepared in a solution of dibromomaleic acid in glacial acetic acid, while stirring, and is further reacted directly with the amine in this solution.

According to a preferred embodiment of process variant (b), the dialkyldihalogenomaleate is prepared from the dihalogenomaleic anhydride and methanol and is reacted with the amine after fractional distillation. Working up is effected as described above (compare U.S. Pat. No. 3,734,927, Example 5).

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, for example against the apple scab causative organism (*Venturia inaequalis*), for combating Leptosphaeria species, such as, for example, the brown spot disease of wheat causative organism (*Leptosphaeria nodorum*), for combating Oomycetes, such as, for example, the leaf rot of potato and tomato causative organism (*Phytophthora infestans*), for combating rice diseases, such as, for example, *Pellicularia sasakii* and *Pyricularia oryzae*, and for combating Puccinia species, for example against the brown rust of wheat causative organism (*Puccinia recondita*).

The fungicidal action against *Cochliobolus sativus* and *Pyrenophora teres* in cereal is also to be mentioned. In appropriate concentrations, the compounds also have an acaricidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts or iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

EXAMPLE 1

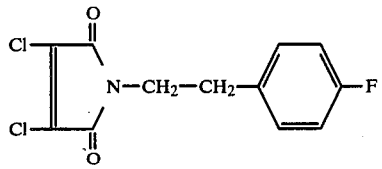

16.7 g (0.1 mol) of dichloromaleic anhydride and 14.0 g (0.1 mol) of 2-(4-fluorophenyl)-ethylamine are stirred in 100 ml of glacial acetic acid at 120° C. for 4 hours. The mixture is cooled to 20° C. and 10 ml of water are added. A colorless precipitate separates out, and is filtered off with suction and dried. 16 g of dichloromaleic acid N-[2-(4-fluorophenyl)-ethyl]-imide of melting point 137°–138° C. are obtained. A further 5.1 g of imide can be isolated by stirring the mother liquor with water. The total yield is 73% of theory.

Example 2

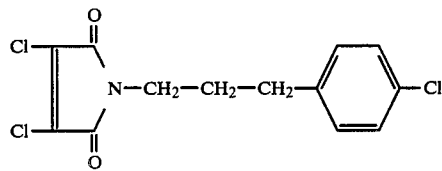

16.7 g (0.1 mol) of dichloromaleic anhydride and 17.0 g (0.1 mol) of 3-(4-chlorophenyl)-propylamine are stirred in 100 ml of glacial acetic acid under reflux for 4 hours. 50 ml of water are added and the mixture is cooled to 20° C. The product is filtered off with suction and dried. 26.1 g (82% of theory) of dichloromaleic acid N-[3-(4-chlorophenyl)-propyl]-imide of melting point 72°–73° C. are obtained.

EXAMPLE 3

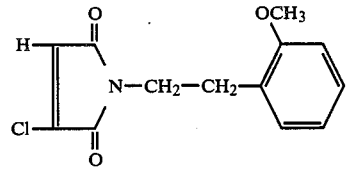

13.25 g (0.1 mol) of chloromaleic anhydride and 15.2 g (0.1 mol) of 2-(2-methoxyphenyl)-ethylamine are heated to the boiling point in 100 ml of glacial acetic acid for 4 hours. 100 ml of water are then added and the oil which has precipitated is extracted with methylene chloride. The methylene chloride phase is separated off, washed with water, dried and evaporated. The oil which remains crystallizes. 20.8 g (78% of theory) of chloromaleic acid N-[2-(2-methoxyphenyl)-ethyl]-imide are obtained.

EXAMPLE 4

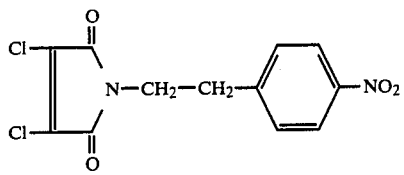

16.7 g (0.1 mol) of dichloromaleic anhydride and 16.5 g (0.1 mol) of (4-nitrophenyl)-ethylamine are stirred in 100 ml of glacial acetic acid under reflux for 4 hours. 100 ml of water are added, the oil which has precipitated is extracted with methylene chloride, the methylene chloride phase is concentrated and the residue is recrystallized from ethanol. 25.4 g (81% of theory) of dichloromaleic acid N-[2-(4-nitrophenyl)-ethyl]-imide of melting point 166° C. are obtained.

EXAMPLE 5

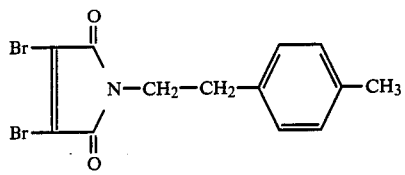

14 g (0.051 mol) of dibromomaleic acid are stirred in 100 ml of glacial acetic acid under reflux for 1 hour. 6.75 g (0.05 mol) of 2-(p-tolyl)-ethylamine are added to the cooled solution of the dibromomaleic anhydride thus prepared and the mixture is stirred under reflux for a further 3 hours. It is cooled to 20° C. and the precipitate is filtered off with suction. After drying, 15.5 g (65% of theory) of dibromomaleic acid N-2-(p-tolyl)-ethylimide are obtained.

The compounds of the formula (I) listed below can be prepared analogously to one of the examples described under 1–5:

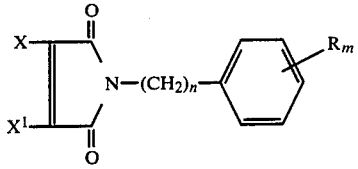

| Example No. | $X_1$ | $X_2$ | n | R | m | Melting point (°C.) |
|---|---|---|---|---|---|---|
| 6 | Cl | Cl | 2 | 2-F | 1 | 121–122 |
| 7 | Br | Br | 2 | 2,6-Cl$_2$ | 2 | 164–168 |
| 8 | Cl | Cl | 2 | 2,4-F$_2$ | 2 | 132–133 |
| 9 | Cl | Cl | 2 | 2-Cl | 1 | 129–130 |
| 10 | Cl | Cl | 2 | 3-Cl | 1 | 141–142 |
| 11 | Cl | Cl | 2 | 4-Cl | 1 | 118–119 |
| 12 | Cl | Cl | 2 | 2-F, 4-Cl | 2 | 122–123 |
| 13 | Cl | Cl | 2 | 2-F, 6-Cl | 2 | 121–122 |
| 14 | Cl | Cl | 2 | 2-Cl, 4-F | 2 | 124–126 |
| 15 | Cl | Cl | 2 | 2,3-Cl$_2$ | 2 | 142–143 |
| 16 | Cl | Cl | 2 | 2,4-Cl$_2$ | 2 | 148–149 |
| 17 | Cl | Cl | 2 | 2,5-Cl$_2$ | 2 | 133–134 |
| 18 | Cl | Cl | 2 | 2,6-Cl$_2$ | 2 | 130–131 |
| 19 | Cl | Cl | 2 | 3,4-Cl$_2$ | 2 | 153–154 |
| 20 | Cl | Cl | 2 | 3,5-Cl$_2$ | 2 |  |
| 21 | Cl | Cl | 2 | 4-Br | 1 | 122–123 |
| 22 | Cl | Cl | 2 | 2-OCH$_3$ | 1 | 108 |
| 23 | Cl | Cl | 2 | 4-OCH$_3$ | 1 | 136–138 |
| 24 | Cl | Cl | 2 | 4-OH | 1 | 175 |
| 25 | Cl | Cl | 2 | 4-OCOCH$_3$ | 1 | 176 |
| 26 | Cl | Cl | 2 | 3,4-(OCH$_3$)$_2$ | 2 | 160–161 |
| 27 | Cl | Cl | 2 | 4-SO$_2$—NH$_2$ | 1 | 213 |
| 28 | Cl | Cl | 2 | 4-NO$_2$ | 1 | 166 |
| 29 | Cl | Cl | 2 | 3-CF$_3$ | 1 | 87–88 |
| 30 | Cl | Cl | 2 | 4-CF$_3$ | 1 | 144–145 |
| 31 | Cl | Cl | 2 | 4-CH$_3$ | 1 | 138–139 |
| 32 | Cl | Cl | 2 | 4-C(CH$_3$)$_3$ | 1 | 130 |
| 33 | Cl | Cl | 3 | 4-Cl | 1 | 72–73 |
| 34 | Cl | Cl | 3 | 4-OCH$_3$ | 1 | oil |
| 35 | Cl | Cl | 3 | 2,3-Cl$_2$ | 2 | 112–116 |
| 36 | Cl | Cl | 3 | 3,4-Cl$_2$ | 2 | 92–95 |
| 37 | Cl | Cl | 3 | 2-Cl | 1 |  |
| 38 | Cl | Cl | 3 | 3-CF$_3$ | 1 |  |
| 39 | Cl | Cl | 3 | 2-F, 4-Cl | 2 | 67–69 |
| 40 | Cl | Cl | 3 | 4-CH$_3$ | 1 |  |
| 41 | H | Cl | 2 | 2-OCH$_3$ | 1 |  |
| 42 | Br | Br | 2 | 4-F | 1 | 156–157 |
| 43 | Br | Br | 2 | 2-F, 4-Cl | 2 | 143–144 |
| 44 | Br | Br | 2 | 4-CH$_3$ | 1 |  |
| 45 | Cl | Cl | 2 | 3-Br, 4-F | 2 | 125–126 |
| 46 | Cl | Cl | 2 | 4-(4-Cl—Phenyl) | 1 | 170–173 |
| 47 | Cl | Cl | 2 | 4-Cyclopentyl | 1 | 127–128 |
| 48 | Cl | Cl | 2 | 3,4-(CH$_3$)$_2$ | 2 | 156–157 |
| 49 | Cl | Cl | 2 | 3,4-(OH)$_2$ | 2 | 164–165 |
| 50 | Br | Br | 2 | 2,4-F$_2$ | 2 | 144–145 |
| 51 | Br | Br | 2 | 3-CF$_3$ | 1 | 111–112 |
| 52 | Br | Br | 2 | 3-Cl | 1 | 159–160 |
| 53 | Br | Br | 2 | 2-F, 6-Cl | 2 | 145–146 |
| 54 | Br | Br | 2 | 2-Cl, 4-F | 2 | 167–168 |
| 55 | Br | Br | 2 | 2,3 Cl$_2$ | 2 | 176–177 |
| 56 | Br | Br | 2 | 4-OCH$_3$ | 1 | 152–153 |
| 57 | Br | Br | 2 | 4-CF$_3$ | 1 | 145–146 |
| 58 | Br | Br | 2 | 4-NO$_2$ | 1 | 189–190 |
| 59 | Br | Br | 2 | 4-OH | 1 | 134–135 |
| 60 | Cl | Cl | 3 | 4-F | 1 | 71–74 |
| 61 | Cl | Cl | 3 | 3Cl | 1 | 97 |
| 62 | Cl | Cl | 2 | 2,4-Cl$_2$, 5-F | 3 | 118–120 |
| 63 | Br | Br | 2 | 2,4-Cl$_2$, 5-F | 3 | 150–153 |
| 64 | Cl | Cl | 2 | 4-N(CH$_3$)$_2$ | 1 | 190–191 |
| 65 | H | Br | 2 | 4-F | 1 |  |
| 66 | H | Br | 3 | 3-Cl | 1 |  |
| 67 | H | Br | 2 | 2,6-Cl$_2$ | 2 |  |

USE EXAMPLES

The compounds shown below are used as comparison substances in the examples which follow:

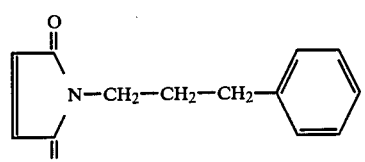

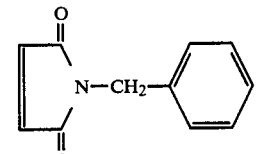

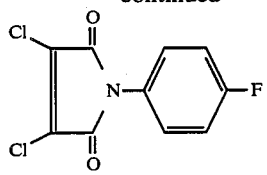 (C)

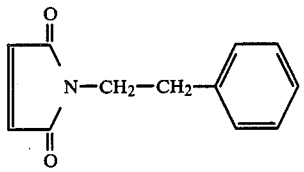 (D)

EXAMPLE A

Puccinia test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples 6, 4, 8 and 1.

EXAMPLE B

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 2, 11, 31, 8, 4, 1 and 30.

EXAMPLE C

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet at 100% relative atmospheric humidity and at about 20° C.

Evaluation is carried out 3 days after the inoculation.

In this test, a clearly superior activity compared the prior art is shown, for example, by the compounds according to the following preparation examples: 11, 18, 9, 16, 31, 27, 22 and 30.

EXAMPLE D

Venturia test (apple)/protective
Solvent:
  4.7 parts by weight of acetone
  0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 33, 11, 6, 18, 16, 19 and 31.

EXAMPLE E

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of *Pyricularia oryzae*. The plants are then placed in a greenhouse at 100% relative atmospheric humidity and 25° C. Evaluation of the disease infestation is carried out 4 days after the inoculation.

In this test, a clearly superior activity compared with the prior art is shown, for example, by the compounds according to the following examples: 19 and 31.

EXAMPLE F

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown in watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 18, 9, 16 and 30.

EXAMPLE G

Pellicularia test (rice)
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the following preparation examples: 11, 6, 32 and 27.

It is understood that the specification and examples are illustrative but not limitative of the present invention and that other embodiments within the spirit and scope of the invention will suggest themselves to those skilled in the art.

We claim:
1. A substituted maleimide of the formula

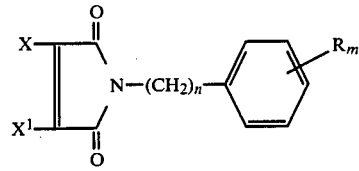

in which
X represents hydrogen, chlorine or bromine,
$X^1$ represents chlorine or bromine,
n represents 2, 3, 4 or 5 and
R represents halogen, alkyl, optionally halogen or alkyl substituted phenyl, phenoxy or $C_5$-$C_6$-cycloalkyl, halogenoalkyl, hydroxyalkyl, alkoxyalkyl, acyloxyalkyl, nitro, cyano, alkoxycarbonyl, alkylcarbonyl, carboxyl, carbonylamino, hydroxyl, alkoxy, halogenoalkoxy, alkanoyloxy, sulphonylamino, alkylsulphonyl, alkylmercapto, mercapto, acylmercapto, halogenoalkylmercapto, amino, mono- or di-alkylamino or alkanoylamino, the various alkyl radicals having 1 to 6 carbon atoms, and m represents 1, 2, 3, 4 or 5.

2. A substituted maleimide according to claim 1 in which
n represents 2, 3 or 4, and
R represents halogen, alkyl with 1 to 6 carbon atoms, or phenyl, $C_5$-$C_6$-cycloalkyl or phenoxy which is optionally mono-, di-, tri-, tetra- or penta-substituted by identical or different halogen or $C_1$-$C_5$-alkyl radicals, or alkoxy, alkoxycarbonyl, alkylcarbonyl or alkylsulphonyl with 1 to 5 carbon atoms per alkyl radical, or carboxyl, carbonylamino, sulphonylamino, nitro, cyano, hydroxyl, halogenoalkyl with 1 to 7 halogen atoms and 1 to 4 carbon atoms per alkyl radical, alkanoyloxy or alkanoylamino with 1 to 5 carbon atoms per alkanoyl radical, amino or mono- or dialkylamino with 1 to 4 carbon atoms per alkyl radical.

3. A substituted maleimide according to claim 1, in which R represents fluorine, chlorine, bromine, alkyl within 1 to 5 carbon atoms, alkoxy with 1 to 4 carbon atoms, sulphonylamino, alkylsulphonyl or alkylcarbonyl with 1 to 3 carbon atoms in the alkyl part, carbonylamino, halogenoalkyl with 1 to 3 carbon atoms and 1 to 5 halogen atoms, phenyl, chlorophenyl, cyclopentyl, cyclohexyl, alkoxycarbonyl with 1 to 4 carbon atoms in the alkoxy part, hydroxyl, acyloxy or acylamino with 1 to 3 carbon atoms per acyl radical, amino, mono- or di-alkylamino with 1 to 3 carbon atoms per alkyl radical or nitro.

4. A substituted maleimide according to claim 1, in which
X and $X^1$ represent chlorine or bromine,
n represents 2 or 3,
R represents fluorine, chlorine, bromine, methyl, ethyl, n-propyl, iso-propyl, n-butyl, sec.-butyl, iso-butyl, tert.-butyl, methoxy, ethoxy, n-propoxy, iso-propoxy, sulphonylamino, methylsulphonyl, ethylsulphonyl, n-propylsulphonyl, isopropylsulphonyl, methylcarbonyl, ethylcarbonyl, n-propylcarbonyl, iso-propylcarbonyl, carbonylamino, trifluoromethyl, phenyl, cyclopentyl, cyclohexyl, methoxycarbonyl, ethoxycarbonyl, n-propoxycarbonyl, iso-propoxycarbonyl, hydroxyl, formyloxy, acetoxy, formylamino, acetamino, amino, methylamino, dimethylamino, ethylamino, diethylamino or nitro, and m represents 1, 2 or 3.

5. A substituted maleimide according to claim 1, wherein such compound is dichloromaleic acid N-[2-(4-fluorophenyl)-ethyl]-imide of the formula

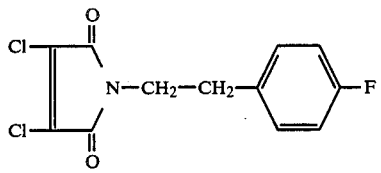

6. A substituted maleimide according to claim 1, wherein such compound is dichloromaleic acid N-[2-(2,4-difluorophenyl)-ethyl]-imide of the formula

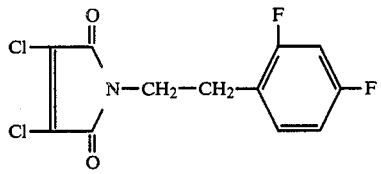

7. A substituted maleimide according to claim 1, wherein such compound is dichloromaleic acid N-[2-(2-chlorophenyl)-ethyl]-imide of the formula

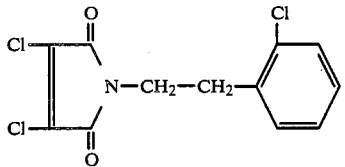

8. A substituted maleimide according to claim 1, wherein such compound is dichloromaleic acid N-[2-(4-chlorophenyl)-ethyl]-imide of the formula

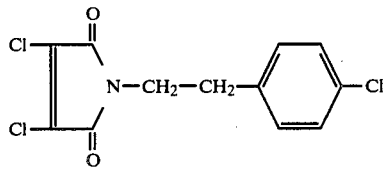

9. A substituted maleimide according to claim 1, wherein such compound is dichloromaleic acid N-[2-(4-trifluoromethylphenyl)-ethyl]-imide of the formula

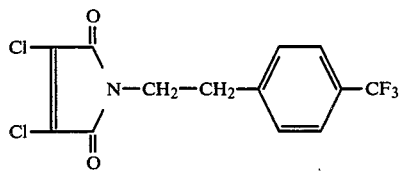

10. A substituted maleimide according to claim 1, wherein such compound is dichloromaleic acid N-[2-(4-methylphenyl)-ethyl]-imide of the formula

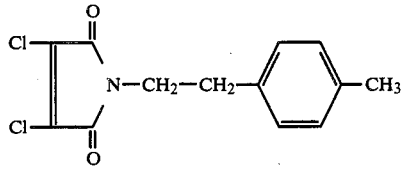

11. A fungicidal composition comprising a fungicidally effective amount of a compound according to claim 1 in admixture with a diluent.

12. A method of combating plant-pathogenic fungi which comprises administering to such fungi or a habitat thereof a fungicidally effective amount of a compound according to claim 1.

13. The method according to claim 12, wherein such compound is
dichloromaleic acid N-[2-(4-fluorophenyl)ethyl]-imide,
dichloromaleic acid N-[2-(2,4-difluorophenyl)ethyl]-imide,
dichloromaleic acid N-[2-(2-chlorophenyl)ethyl]-imide,
dichloromaleic acid N-[2-(4-chlorophenyl)ethyl]-imide,
dichloromaleic acid N-[2-(2-(4-trifluoromethylphenyl)ethyl]-imide or
dichloromaleic acid N-[2-(4-methylphenyl)ethyl]-imide.

* * * * *